(12) United States Patent
Heinonen

(10) Patent No.: US 6,983,750 B2
(45) Date of Patent: Jan. 10, 2006

(54) METHOD FOR INDICATING THE AMOUNT OF VENTILATION INHOMOGENEITY IN THE LUNG

(75) Inventor: Erkki Heinonen, Helsinki (FI)

(73) Assignee: Instrumentarium Corp., (FI)

(*) Notice: Subject to any disclaimer, the term of this patent is extended or adjusted under 35 U.S.C. 154(b) by 0 days.

(21) Appl. No.: 10/650,114

(22) Filed: Aug. 26, 2003

(65) Prior Publication Data
US 2005/0045180 A1 Mar. 3, 2005

(51) Int. Cl.
*A61M 16/00* (2006.01)
*A62B 7/00* (2006.01)
*F16K 31/02* (2006.01)

(52) U.S. Cl. .............. 128/204.22; 128/205.11; 128/203.14; 128/203.25; 600/532

(58) Field of Classification Search .......... 128/204.18, 128/204.21, 204.22, 204.23, 204.26, 204.29, 128/205.11, 203.12, 203.14, 203.25, 205.13, 128/205.14, 205.17, 200.26, 200.15; 600/529, 600/532
See application file for complete search history.

(56) References Cited

U.S. PATENT DOCUMENTS

| | | | | |
|---|---|---|---|---|
| 3,726,270 | A | * | 4/1973 | Griffis et al. ............... 600/532 |
| 5,540,233 | A | * | 7/1996 | Larsson et al. ............ 600/538 |
| 5,615,669 | A | | 4/1997 | Olsson et al. |
| 6,139,506 | A | * | 10/2000 | Heinonen ................... 600/532 |
| 6,254,546 | B1 | | 7/2001 | Viertö-Oja |
| 6,315,739 | B1 | | 11/2001 | Merilianen et al. |
| 2002/0052560 | A1 | | 5/2002 | Koch et al. |

FOREIGN PATENT DOCUMENTS

| | | |
|---|---|---|
| EP | 0 791 327 | 8/1997 |
| WO | WO 02/24070 | 8/2002 |

OTHER PUBLICATIONS

*A new method for non-invasive, manoeuvre-free determination of "static" pressure-volume curves during dynamic/therapeutic mechanical ventilation,* S. Karason et al., Acta Anaesthesiol Scand. 2000; 44; 578-585, Printed in Denmark.

* cited by examiner

*Primary Examiner*—Henry Bennett
*Assistant Examiner*—Andrea M. Ragonese
(74) *Attorney, Agent, or Firm*—Andrus, Sceales, Starke & Sawall, LLP

(57) ABSTRACT

A method of determining ventilation inhomogeneity in the lungs is provided. During the first step of the method, a lung volume series is calculated from a series of measured lung inert gas concentrations and lung inert gas volumetric change measured data series. As a second step, the series of lung volumes is completed with a series of value representing the total gas exchange efficiency in the lungs. A global inert gas dilution ratio may be used for this purpose. The gas exchange efficiency values are such that less ventilation is represented by lower numbers. As the third step, the gas exchange efficiency series is plotted as an ordinate and lung volume series as an abscissa to form a graph. From this graph both the lung volume and homogeneity of ventilation become directly apparent.

7 Claims, 2 Drawing Sheets

US 6,983,750 B2

METHOD FOR INDICATING THE AMOUNT OF VENTILATION INHOMOGENEITY IN THE LUNG

BACKGROUND OF THE INVENTION

The present invention is directed to a method for indicating ventilation efficacies occurring in the lungs of a subject and the volumetric portions of the lungs possessing differing ventilation efficacies. Such information is useful in determining the uniformity or homogeneity, or lack thereof, in the ventilation occurring in the subject's lungs. The method may also be used to determine the volume of the lungs.

When breathing gases are inspired by a subject and pass from the patient airways into the lungs, the inspired breathing gases travel in the direction of the least flow impediment, of highest lung elasticity, and of smallest gas flow resistance. The lungs are always inhomogeneous with respect to these factors, and therefore the distribution of the inspiration gas flow into, or ventilation of, the lungs is uneven.

When a given volume of inspired breathing gas $V_A$ flows into a lung compartment of volume V, the ventilation of that compartment is defined as $V_A/V$. The smaller the inspired gas volume $V_A$ entering a given compartment, compared to the compartment volume V, i.e. the lower the $V_A/V$ value, the smaller will be the amount of blood flow for which that compartment can provide adequate oxygenation and carbon dioxide removal and, thus, the less effective, or efficacious, this lung compartment will be in these basic functions of respiration. In mathematical treatment and analysis of the lung, the categorizations of lung characteristics employed in/resulting from such treatments are often expressed as "compartments," as the term is used above. It is to be understood that such compartmental descriptions are analytical concepts that do not necessarily have any direct correlation to anatomical portions of the lungs, such as lobes. The gases in a given compartment are considered perfectly mixed.

When the lungs are healthy, lung ventilation is sufficiently homogeneous throughout the lung for the physiological gas transfer requirements of the subject. However, the situation changes significantly with various lung diseases that may cause the ventilation $V_A/V$ in portions of the lungs to be as small as 1/100 or even 1/1000. When there is little, or no, ventilation in a portion of the lungs, but blood flow or perfusion is present, a "shunt" is said to exist in the lung in which gas/blood transfer is lessened or eliminated. Venous blood, i.e. unoxygenated blood from the shunt, becomes mixed with oxygenated and $CO_2$ depleted blood from properly functioning parts of the lungs. This reduces the total blood oxygenation/$CO_2$ elimination carried out in the lungs.

During inspiration, a lung compartment fills with the inspired gas volume $V_A$ and a practically equal volume of breathing gases is removed during expiration, although normally $O_2$ uptake into blood is a little larger than $CO_2$ release from blood. Assume for simplicity that a lung compartment has a concentration $F_o$ of a particular gas, such as nitrogen, that is not readily exchanged with blood. For a steady state of breathing, the concentration in the lungs will be the same as the concentration in the inspired breathing gases. The concentration F of the gas in a compartment after inspiration has occurred is $$F = F_0 \cdot \frac{V}{V + V_A} \qquad (1)$$

The term $V/(V_A+V)$ is a dilution factor, or the ratio of the new compartment concentration F after inspiration of volume $V_A$ to the concentration $F_o$ in the compartment before ventilation. The more the compartment is ventilated, the lower the new compartment concentration F will be and the smaller the number of breaths needed to deplete the compartment of the gas, and vice versa. For explanatory purposes, a gas, such as nitrogen, is termed herein an "inert" gas, although it is recognized there may be some transfer to/from the blood in the lungs depending on the relative amounts of the gas in the inspired breathing gases and in the blood. However, the exchange occurring with the blood is negligible compared to that occurring from ventilation.

As the subject is usually ventilated by the aid of a mechanical ventilator, the inspired breathing volume $V_A$ may be determined from the ventilator. Or the volume may be directly measured as it is inspired by the patient.

Lung volume V can be measured by an inert gas elimination technique. In this method the lungs are first ventilated with a breathing gas mixture of known composition and containing an inert gas. At a steady state condition, i.e. the state where the expired gas composition is unchanged from breath to breath, a sudden change in the inspired gas mixture inert gas content is initiated. The expired inert gas concentrations and volumes are analyzed for the breaths following the sudden change. Lung volume V is then calculated from this data as:

$$\text{Lung Volume } V = \frac{\sum_{breaths} \Delta V_{ig}}{F - F_0} \qquad (2)$$

where ($\Delta V_{ig}$) is the change in expired inert gas volume in the lungs for a single, given breath, F is the inert gas concentration of the lungs after the latest breath, and $F_0$ is the steady state inert gas concentration before the inert gas change was initiated. The lung inert gas concentrations F may be conveniently determined as the end tidal breathing gas concentrations of the subject. The lung volume V measured by Equation 2 is the physical, anatomical volume of the lungs.

Typically the inert gas used for the analysis is nitrogen ($N_2$) as described above, but also helium (He), sulfur hexafluoride ($SF_6$), and fluoropropane (US 2002/0052560) may be used.

The above volume measurement technique, carried out for a number of breaths, forms a data series for the inert gas concentrations F in the lungs and for single breath inert gas volume changes $\Delta V_{ig}$. These data series have also been used to analyze the homogeneity, or inhomogeneity, of lung ventilation. Some indices of lung homogeneity/inhomogeneity are based on analysis of the rate of change of inert gas concentration as related to gas turnovers. The term "turnover" describes the relationship between ventilation volume $V_A$ and lung volume. For example, if a single compartment lung has a volume of 3000 ml and the ventilation volume $V_A$ is 500 ml, a turnover is six breaths. Other indices follow the rate of change of total expired inert gas volume.

In each of these methods the resulting index is a number having an abstract scale, which is not related to clinically important, self-explanatory terms, such as lung volume or ventilation efficacy. Therefore, although these indices may have good correlation with ventilation inhomogeneity, they have not gained clinical acceptance.

Another problem with these methods is that in real multi-compartment lungs, the data series for the F and $\Delta V_{ig}$ values often represent different change response patterns, and when only one of these factors is considered, some part of the information will be lost.

The inhomogeneity of the lung ventilation is as important a parameter as the lung volume itself since in various diseases, part of the lung volume may have insufficient ventilation for the needed of blood/gas transfer. Therefore, it is important to know not only the lung volume, but also how well this volume is utilized, i.e. ventilated. Knowing this information will give a clinician new tools for optimizing ventilation and utilizing other patient therapies by giving a direct indication of the response of the subject to the measures taken to improve the lung function. It is further desirable that presentation of the information be self-explanatory to the clinician

SUMMARY OF THE INVENTION

In the method of the present invention, lung inhomogeneity is considered in terms of lung volume and related gas exchange efficiency or efficacy. By "gas exchange efficiency" or "gas exchange efficacy" is meant the effectiveness by which breathing gases flow into and out of the lungs, which flow is commonly termed the ventilation of the lungs. It does not refer to the transfer of gases to and from the blood.

The method of the present invention has two advantages. First, both the data series for the inert gas concentration F and the data series for the single breath change in inert gas volume $\Delta V_{ig}$ collected during the course of inert gas measurement over a series of breath are used. This is in contrast to the prior art techniques, noted above, that used one or the other of the data series. The method of the present invention is advantageous because the concentration data F is more sensitive to the ventilation of the major compartments of the lung whereas the $\Delta V_{ig}$ data responds also to the less significant compartments of the lung. And second, the outcome is given in terms of lung volume and gas exchange efficacy, which quantities are readily usable by the clinician.

During the initial steps of the method of the present invention, a lung volume V series is calculated from a series of measured lung inert gas concentrations F and lung inert gas volumetric changes $\Delta V_{ig}$. This may be accomplished through use of the inert gas elimination technique and Equation 2, above.

In subsequent steps, the lung volumes V data series is completed, or matched, with a representation of the total gas exchange efficiency of the lungs. A convenient way of doing this is to employ the lung volume V values, along with the inspired breathing gas volumes $V_A$ to obtain a global dilution factor for the lung. One such dilution factor is described above in connection with Equation 1 with the quantity $V_A$ being the cumulative volume of the inspired breathing gases to each breath in the data series.

It is important from the standpoint of clarity to present the reductions in the efficacy of ventilation with reducing numerical values, so that lung volumes where the gas exchange approaches zero are represented with a numerical values also approaching zero. Therefore, in the concluding steps of the method of the present invention, the volume series and the gas exchange efficiency values are presented in such a manner. A convenient way of doing this is to plot the gas exchange efficiency series as an ordinate and lung volume series as an abscissa to form a graph. From this graph both the lung volume and homogeneity of ventilation become directly apparent and self-evident.

BRIEF DESCRIPTION OF THE DRAWINGS

The invention is further described below with the aid of following figures in which.

DETAILED DESCRIPTION OF THE INVENTION

In the preferred embodiment of the present invention described in detail below, a method for determining lung inhomogeneity is described. It should be understood that the drawings and specification are to be considered an exemplification of the principles of the invention, which is more particularly defined in the appended claims.

Figure 2:
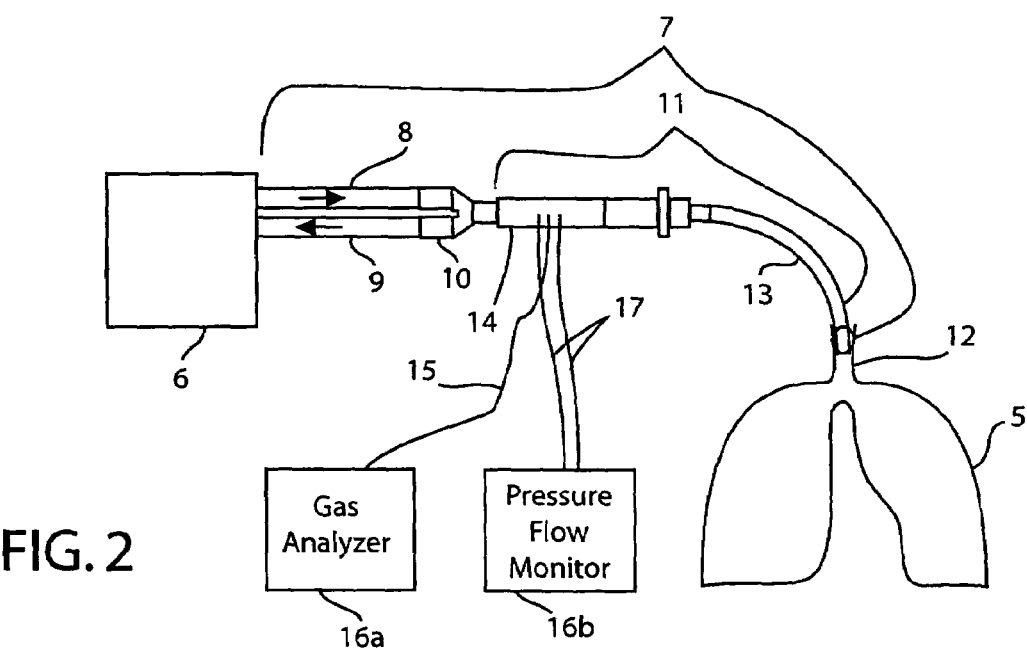
FIG. 2 shows apparatus suitable for carrying out the method of the present invention.

Referring to FIG. 2, a ventilation therapy apparatus is shown in which a patient's lungs 5 are connected to ventilator 6 via breathing circuit 7. The breathing circuit 7 comprises inspiration limb 8, expiration limb 9, Y-piece 10, and patient limb 11. During the inspiratory phase of a respiratory cycle, pressurized inspiration breathing gases of a desired composition are conducted from ventilator 6 through the inspiration limb 8, to Y-piece 10 and further through patient limb 11 to patient airways 12 and lungs 5. During inspiration, ventilator 6 closes the expiration limb 9 with an expiration valve (not shown) located within ventilator 6 to force the pressurized breathing gas flow from ventilator 6 to lungs 5. During the expiratory phase of the respiratory cycle, inspiration gas flow is stopped, and the ventilator control system opens the expiration valve. The elasticity of the patient's lungs and external pressure exerted by the patient's chest wall on the lungs force the breathing gases to flow out from the lungs 5 to patient airways 12, patient limb 11, Y-piece 10, and expiration limb 9 and to ventilator 6. It is also possible to use ventilator 6, or other appropriate means, with a spontaneously breathing patient in which case the action of the patient's chest controls the respiration and the ventilator or other means controls the composition of the breathing gases.

Patient limb 11 includes an endotracheal tube 13 that transports the gases between upper airways 12 and Y-piece 10. A flow sensor 14 and sampling point for gas analyzer gas sampling line 15 of gas analyzer 16a and other components may be connected to patient limb 11. Breathing circuit pressure and the breathing gas flow can be measured through pressure sensors located in monitor 16b connected to the patient limb with the pressure lines 17.

Figure 1:
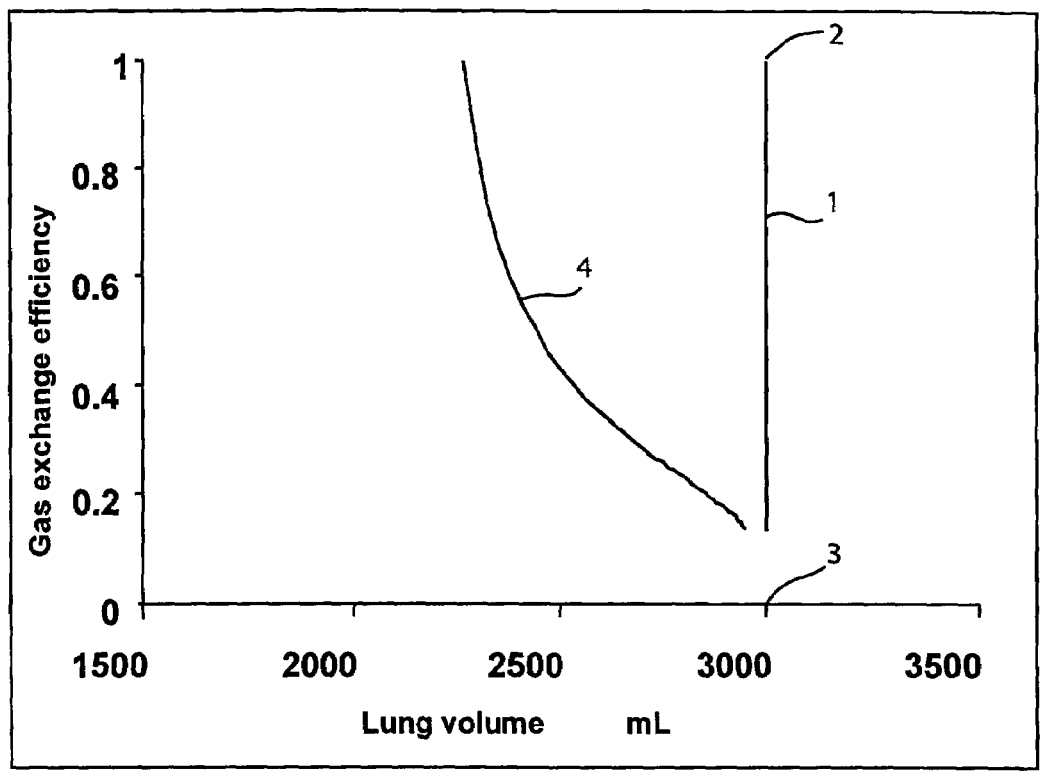
FIG. 1 is a graph showing theoretical background for the method of the present invention.

The method of the invention will be more fully appreciated from the following example and with reference to FIG. 1, in which a one compartment lung model and a two compartment lung model are considered. Each model has a total volume V of 3000 ml and a tidal ventilation volume $V_A$ of 500 ml. In FIG. 1, a graph is shown in which the abscissa represents lung volume and the ordinate assigns the relative gas exchange efficiency regarding a particular lung volume.

In a one compartment lung, both the change in the inert gas volume in the lung $\Delta V_{ig}$ and the change in the inert gas concentration F follow the same exponential change pattern. The lung volume as determined by Equation 2, will thus have a constant value from the very first breath. This is indicated with the vertical line 1 in FIG. 1. Because any further ventilation of the lungs does not detect any more volume, the vertical line will result at the lung volume of 3000 ml, as shown at 3. Assuming no inhomogenieties exist, all the volume is fully ventilated or has the highest gas exchange efficiency. This is represented by the termination of the top of the line 1 at the height of the abscissa, i.e. at point 2.

A two-compartment model graph is presented by the curve 4 in FIG. 1 which compartments each have equal volumes of 1500 ml but one compartment is ventilated with 400 ml of the breathing gases/breath and the other compartment is ventilated with a 100 ml tidal volume of breathing gases/breath. The result in this case is the convex line 4 obtained as follows. From the data for a first breath, or starting point, following a change in inert gas concentration, and by use of Equation 2, the lung volume determined or "found" is 2260 ml. This initial determination indicates that the best-ventilated lung volume having the highest gas exchange efficiency is about 2260 ml.

This lung volume value is then used to determine an overall or global gas exchange efficacy or dilution ratio for the series of data obtained from subsequent breaths. For example, the dilution ratio may be calculated according to Equation 1, given above, as $V/(V+V_A)$ or $2260/(2260+500) = 0.82$ where V is the determined lung volume and $V_A$ is the inspired volume of breathing gases. This value is assigned as the best gas exchange efficacy found in the lungs, and is used for the following breaths to normalize the efficacies to this best value. That is, this value is used as the reference value for normalization of any following breath to obtain the relative gas exchange efficiency of any compartment as related to the best-ventilated compartment. The use of normalization and a relative scale is advantageous in facilitating data comparison, as for example among tests at different times on the same patient or among tests performed on different patients. However normalization is however not necessary for the practice of the invention.

For the next breath after the first breath or starting point, a new gas exchange efficacy is calculated by using the newly measured lung volume and the sum of breathing gases volumes $V_A$ provided to the lungs since the change in inert gas concentration. This value, either normalized or unnormalized, is assigned to this breath along with the newly measured lung volume. These steps are continued until lung volume no longer increases, i.e. until no more lung volume is "found."

For example, after about one lung volume turnover, that is, after the fifth breath, when the total ventilation $V_A$ to the subject for the five breaths is 2500 ml, the volume "found" in the lung is 2380 ml and the gas exchange efficiency is 0.49/0.82=0.60, and further on at three turnovers, the numbers are 2670 ml and 0.25/0.82=0.31. Finally, at seven turnovers, lung volume is found to be 2930 ml and the relative gas exchange efficiency at is 0.31/0.82=0.16.

The foregoing pattern in gas exchange efficiency data is due to the differences in ventilation, or gas exchange efficacies, of the compartments of the lungs. During the first breaths of a sequence of breaths, the compartment of good ventilation and high gas exchange is depleted rapidly of the inert gas whereas the gas remains in the other compartment with low ventilation. Once the effectively ventilated compartment becomes depleted of the gas, the depletion from the less effectively ventilated compartment continues. This is seen as a further volume depletion associated with less significant changes in inert gas concentration, the magnitude of which is dominated by the more effectively ventilated compartment of the lungs. The volume of the less effectively ventilated compartment becomes more visible and becomes "found" by the method of the present invention.

From the standpoint of gas transfer between the blood and the breathing gases, the physiological benefit to the subject of lung compartments of lowest gas exchange efficiency, i.e. the last "found" compartment, may be questionable. However, they represent a volume of the lung having a potential for increased gas exchange, as by responding to therapies initiated by a clinician attending the subject following a study of the data produced by the method of the present invention.

Although the foregoing example is an over simplification of actual lungs in which the ventilation of different compartments may differ by orders of magnitude from each other, the example gives an understanding of the use, simplicity, and the self-evident nature of the method of the present invention.

Further, also for purposes of simplicity, the example considers the inspired gas inert gas concentration as initially zero, which is not necessary for the invention as, for example, in the case in which nitrogen is used as the inert gas. Also, the change in magnitude of the inert gas may be upwards or downwards from the steady state level. For example, for nitrogen, a reduction in the amount of inert gas may be accomplished by adjusting the composition of the breathing gases provided by ventilator 6. Typically the breathing gases are a mixture of air and pure oxygen supplied at a constant flow rate to breathing circuit 7. Increasing the amount of oxygen provided by the ventilator will reduce the amount of air, and hence nitrogen, provided to the subject since the overall flow rate remains constant. For a gas such as sulfur hexafloride, a gas injector would be provided in ventilator 6. If a small change in inert gas is applied, it will be apparent that, with the smallest change, the measurement resolution may be insufficient for the needs of the measurement. For example, when using nitrogen as the inert gas, the step is advantageously 5% or larger, but with $SF_6$ changes as small as 0.5% may be applied.

Ordinary measurement instrumentation used in clinical application usually do not include means to measure nitrogen directly. However, this measurement can be carried out when the composition of the breathing gases is known, and the percentages of the gases other than nitrogen are also known. The percentages sum up to 100% and the rest of the gas over the measured oxygen, $CO_2$ and possibly also $N_2O$ and anaesthetic gases, is nitrogen. Using other inert gases, appropriate measurement instrumentation is provided in gas analyzer 16a.

Also, it is possible to employ the measured lung volume V and inspired breathing gas volume $V_A$ in other manners than that described above in connection with Equation 1 to obtain a useful dilution ratio or indication of gas exchange efficiency. For example, the quantity $V/\Sigma V_A$ or the product of the dilution rations $(V/(V+V_A))$ for all commenced breaths, i.e. the product $(V/(V+V_A^N))$, where N is from the first to the last breath in the series, may be used.

Figure 3:
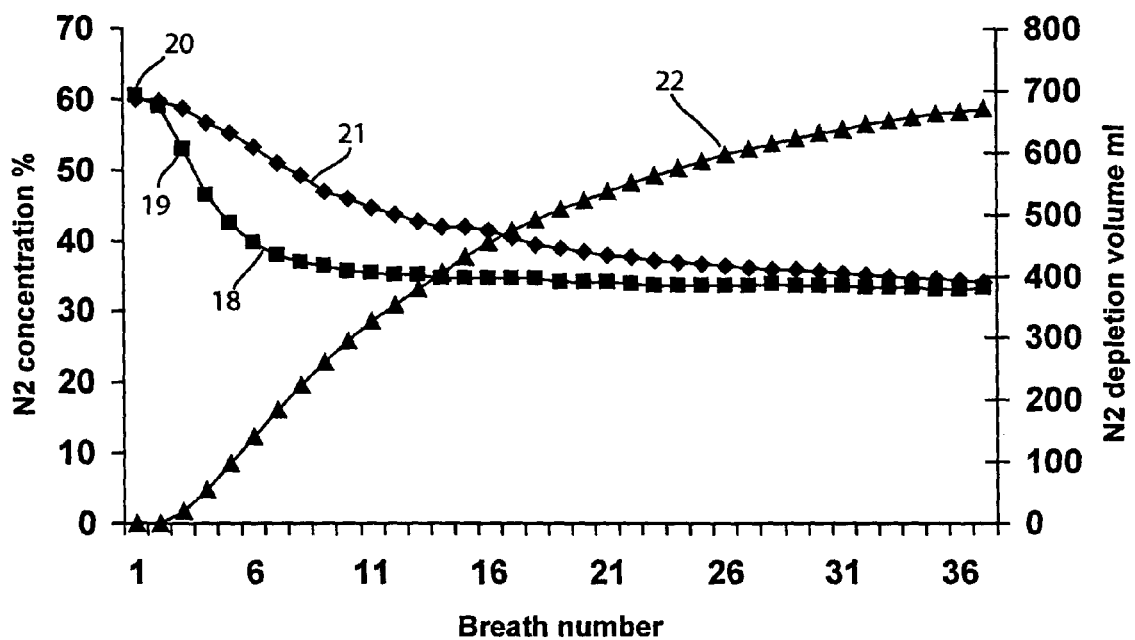
FIG. 3 shows gas measurement that could typically be obtained in the course of carrying out the method of the present invention.

Inert gas measurement curves are presented in FIG. 3 as an example of the course of the measurements employed in the method of the present invention using nitrogen as the inert gas. A step reduction in the inspired gas nitrogen concentration 18 starts at breath three (3) as at 19. Before the step reduction in the nitrogen concentration, the initial value of the nitrogen concentration 20 is determined as the nitrogen concentration of the inspired breathing gases before the change was initiated. These values are related to the left-hand scale of FIG. 3. Assuming steady state conditions, the concentration $F_o$ of nitrogen in the lungs before the step reduction is the same as that of the inspired breathing gases. Because of factors such as anatomical dead spaces in the subject and the volume of breathing circuit 7, the form of graph 18 has that shown in FIG. 3, notwithstanding a step reduction in inspired nitrogen concentration. Also, because of operational limitations in ventilator 6, as a practical matter, the reduction in nitrogen concentration may actually occur over several breaths, i.e. as a ramp not a step.

The graph 21 is the nitrogen concentration F of the lungs, as measured by the expired tidal volume. The nitrogen volume expired or "washed out" from the lungs is indicated by the reference numeral 22 in FIG. 3 and is related to the right-hand scale. It follows, with delay, the change in inspired nitrogen concentration at 19 and is the amount of nitrogen removed from the lungs to reduce the lung nitrogen concentration from the 60% shown at 20 to the new level of 35% found in the right-hand portion of FIG. 3.

As noted above from Equation 2, the lung volume V is calculated for any particular breath by dividing the nitrogen volume depleted or washed out from the lungs since commencing the change in the inspired nitrogen concentration with the reduction of expired nitrogen concentration from the initial value. The gas exchange efficiency for that particular breath concentration is also determined, also as explained above.

Figure 4:
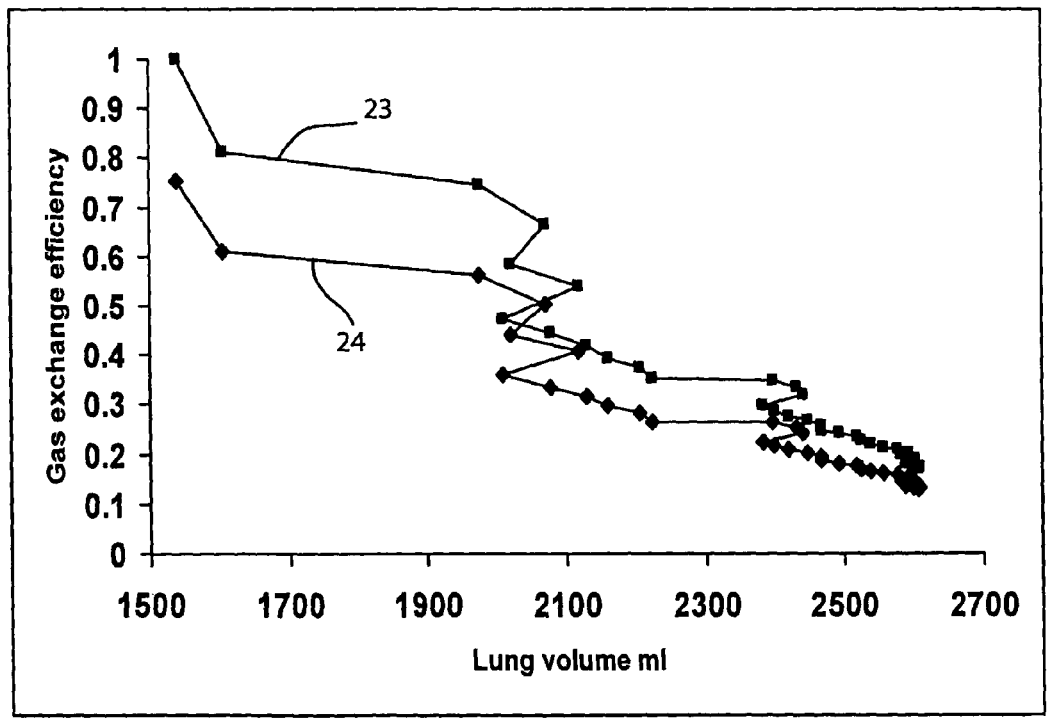
FIG. 4 shows a lung volume and inhomogeneity analysis obtained from data of the type shown in FIG. 3.

Gas exchange efficiency is then plotted as ordinate and the lung volume as abscissa to get the graphical presentation 23 and 24 of the relationship between gas exchange efficiency distribution and lung volume as presented on FIG. 4. The graph 23 shows normalized data, i.e. a graph in which the highest gas exchange efficiency has a nominal value of 1. The graph 24 shows un-normalized data. Graphs 23 and 24 are thus more realistic examples of the lung data shown by the graph 4 in FIG. 1 for a simplified two compartment lung. The graphic representation of the relationship between gas exchange efficiency and lung volume shown in FIG. 4 may be used by the clinician in assessing and treating the subject.

While this invention is susceptible to embodiments in many different forms, the drawings and the specification describe in detail a preferred embodiment of the invention. They are not intended to limit the broad aspects of the invention to the embodiment illustrated.

What is claimed is:

1. A method for determining gas exchange efficiencies of volumetric portions of and the volume of the lungs of a subject to express ventilation homogeneity characteristics of volumetric portions of the lungs, said method comprising the steps of:
   (a) allowing the patient to breathe with breathing gases having given properties regarding the amount of an inert gas contained therein;
   (b) ascertaining the concentration $F_o$ of the inert gas in the lungs of the subject;
   (c) altering the amount of the inert gas in the breathing gases provided to the subject;
   (d) causing the subject to breathe breathing gases having the altered amount of the inert gas;
   (e) thereafter measuring the change in volume $\Delta V_{ig}$ of the inert gas in the lungs of the subject and the concentration F of inert gas in the lungs of the subject for each breath;
   (f) making a determination of the lung volume V of the subject using a summation of the volume change $\Delta V_{ig}$ of the inert gas in the lungs of the subject, the concentration F of the inert gas in the lungs of the subject, and the amount $F_o$ of the inert gas in the breathing gases ascertained in step (b);
   (g) obtaining a measure of the gas exchange efficiency of the subject's lungs using the breathing gas volume $V_A$ of the subject and the lung volume V determined in step (f);
   (h) repeating step (e) and, respectively, steps (f) and (g) for a subsequent breath of the subject to make at least one further determination of the lung volume V of the subject and obtain at least one further gas exchange efficiency measure;
   (i) forming a lung volume V data series comprising the volumes V determined for each breath and, respectively, a gas exchange efficiency data series comprising gas exchange efficiencies obtained for each breath; and
   (j) expressing the ventilation homogeneity of volumetric portions of the lungs of the subject by relating the series of gas exchange efficiencies to the lung volume series.

2. The method according to claim 1 wherein step (e) is further defined as measuring the concentration F of the inert gas in the lungs of the subject using end tidal inert gas concentrations of the subject.

3. The method according to claim 1 wherein step (g) is further defined as obtaining a gas exchange efficiency measure comprising a dilution ratio for the amount of inert gas $F_o$ in the breathing gases.

4. The method according to claim 1 wherein step (j) is further defined as carrying out the expression graphically by plotting one data series on an abscissa of a graph and the other data series on an ordinate of a graph.

5. The method according to claim 1 wherein step (h) is further defined as making a plurality of further determinations of lung volume V and as obtaining a plurality of further gas exchange efficiency measures.

6. The method according to claim 1 further including the step (k) of normalizing the further gas exchange efficiency measure obtained in step (h) using the gas exchange efficiency measure obtained in step (g) for a first breath of the subject after altering the amount of inert gas in the breathing gases provided to the subject.

7. The method according to claim 5 further including the step (k) of normalizing the further gas exchange efficiency measure obtained in step (h) using the gas exchange efficiency measure obtained in step (g) for a first breath of the subject after altering the amount of inert gas in the breathing gases provided to the subject.

* * * * *